United States Patent
Wang

(10) Patent No.: US 8,377,533 B2
(45) Date of Patent: *Feb. 19, 2013

(54) BIOABSORBABLE STENT WITH LAYERS HAVING DIFFERENT DEGRADATION RATES

(75) Inventor: Yunbing Wang, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/269,380

(22) Filed: Oct. 7, 2011

(65) Prior Publication Data

US 2012/0089221 A1    Apr. 12, 2012

Related U.S. Application Data

(63) Continuation of application No. 12/036,872, filed on Feb. 25, 2008, now Pat. No. 8,057,876.

(51) Int. Cl.
*A61F 2/06* (2006.01)
*B32B 1/08* (2006.01)
*B32B 27/08* (2006.01)
*B32B 27/36* (2006.01)

(52) U.S. Cl. .................. 428/36.91; 428/35.7; 623/1.38; 623/1.44; 623/1.49

(58) Field of Classification Search .................. 428/34.1, 428/35.7–36.2, 36.4, 36.9, 36.91; 623/1.1, 623/1.15–1.22, 1.38, 1.42–1.54
See application file for complete search history.

(56) References Cited

U.S. PATENT DOCUMENTS

| | | | |
|---|---|---|---|
| 6,379,379 B1 | 4/2002 | Wang |
| 6,821,295 B1 | 11/2004 | Farrar |
| 7,029,495 B2 | 4/2006 | Stinson |
| 7,166,134 B2 | 1/2007 | Datta et al. |
| 8,057,876 B2 | 11/2011 | Wang |
| 2004/0044397 A1 | 3/2004 | Stinson |
| 2004/0193255 A1 | 9/2004 | Shanley et al. |
| 2007/0078513 A1 | 4/2007 | Campbell |
| 2007/0106371 A1 | 5/2007 | Datta et al. |
| 2007/0254012 A1 | 11/2007 | Ludwig et al. |

FOREIGN PATENT DOCUMENTS

| WO | WO 2004/026361 | 4/2004 |
| WO | WO 2007/140320 | 12/2007 |

OTHER PUBLICATIONS

International Search Report for PCT/US2009/033686 mailed Apr. 16, 2010, 7 pgs.

*Primary Examiner* — Walter B Aughenbaugh
(74) *Attorney, Agent, or Firm* — Squire Sanders (US) LLP

(57) ABSTRACT

A bioabsorbable stent and method of forming the same including a stent scaffolding formed from polymer layers with different degradation rates is disclosed. The polymer layers include an abluminal layer, a luminal layer, and optionally one or more middle layers. A degradation rate of the layers increases from the luminal layer to the abluminal layer.

8 Claims, 5 Drawing Sheets

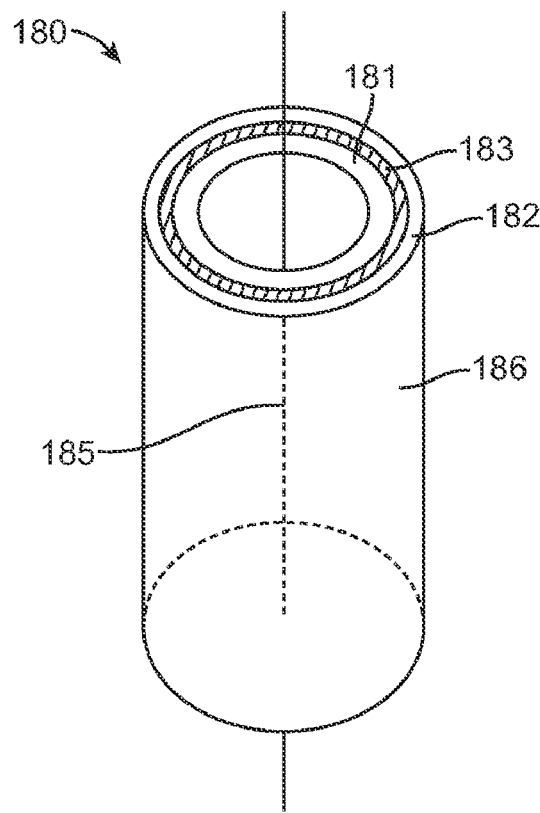
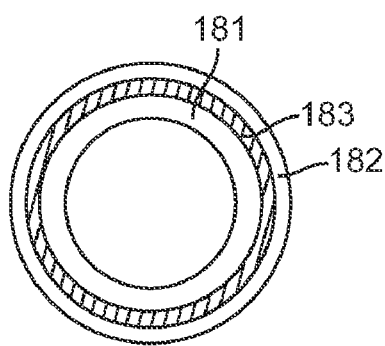
FIG. 4A
FIG. 4B
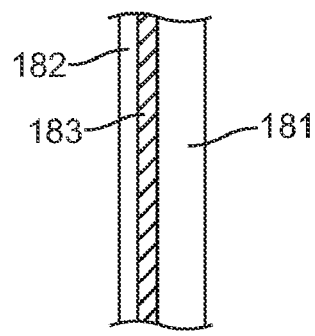
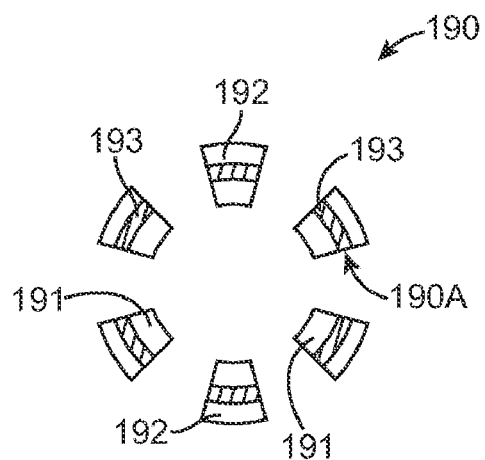
FIG. 4C
FIG. 5

BIOABSORBABLE STENT WITH LAYERS HAVING DIFFERENT DEGRADATION RATES

This application is a continuation of U.S. patent application Ser. No. 12/036,872 filed Feb. 25, 2008, U.S. Pat. No. 8,057,876, which is incorporated by reference herein.

BACKGROUND OF THE INVENTION

1. Field of the Invention

This invention relates to bioabsorbable polymer stents with layers having different degradation rates.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

SUMMARY OF THE INVENTION

Various embodiments of the present invention include a bioabsorbable stent comprising a stent scaffolding comprising: an abluminal layer, a luminal layer, and optionally one or more middle layers, each layer comprising a glassy degradable polymer of the same chemical composition, wherein the abluminal layer is an outermost radial layer of the stent scaffolding with an outer surface contacting a vessel wall upon implantation, wherein the luminal layer is an innermost radial layer of the stent scaffolding with an inner surface contacting an inner lumen of the vessel upon implantation, wherein the molecular weight of the polymer of the luminal layer is higher than the molecular weight of the polymer of the abluminal layer, and wherein the molecular weight of the polymer of the layers decreases between each of the layers from the luminal layer to the abluminal layer so that the degradation rate of the layers increases between each of the layers from the luminal layer to the abluminal layer.

Further embodiments of the present invention include a bioabsorbable stent comprising a stent scaffolding including: an abluminal layer, a luminal layer, and optionally at least one middle layer, wherein the abluminal layer is an outermost radial layer of the stent scaffolding with an outer surface contacting a vessel wall upon implantation, wherein the luminal layer is an innermost radial layer of the stent scaffolding with an inner surface contacting an inner lumen of the vessel upon implantation, wherein the luminal layer comprises PLLA or PLGA and the abluminal layer and the optional at least one middle layer comprises PLGA, wherein the GA content of the abluminal layer is higher than the GA content of the luminal layer, and wherein the GA content of the polymer of the layers increases between each of the layers from the luminal layer to the abluminal layers so that the degradation rate between each of the layers increases between each of the layers from the luminal layer to the abluminal layer, wherein the stent scaffolding comprises a middle layer.

BRIEF DESCRIPTION OF THE DRAWINGS

FIG. 4A depicts a perspective view of a tube.

FIG. 4B depicts a radial cross-section of the tube of FIG. 4A.

FIG. 4C depicts a cross-section of the wall of the tube of FIG. 4A parallel to its cylindrical axis.

FIG. 5 depicts a radial cross-section of a stent scaffolding cut from a tube.

DETAILED DESCRIPTION OF THE INVENTION

Embodiments of the present invention relate to stents having a biodegradable body composed of layers with different degradation rates. These embodiments are applicable to self-expandable stents, balloon-expandable stents, stent-grafts, and generally tubular medical devices.

Figure 1:
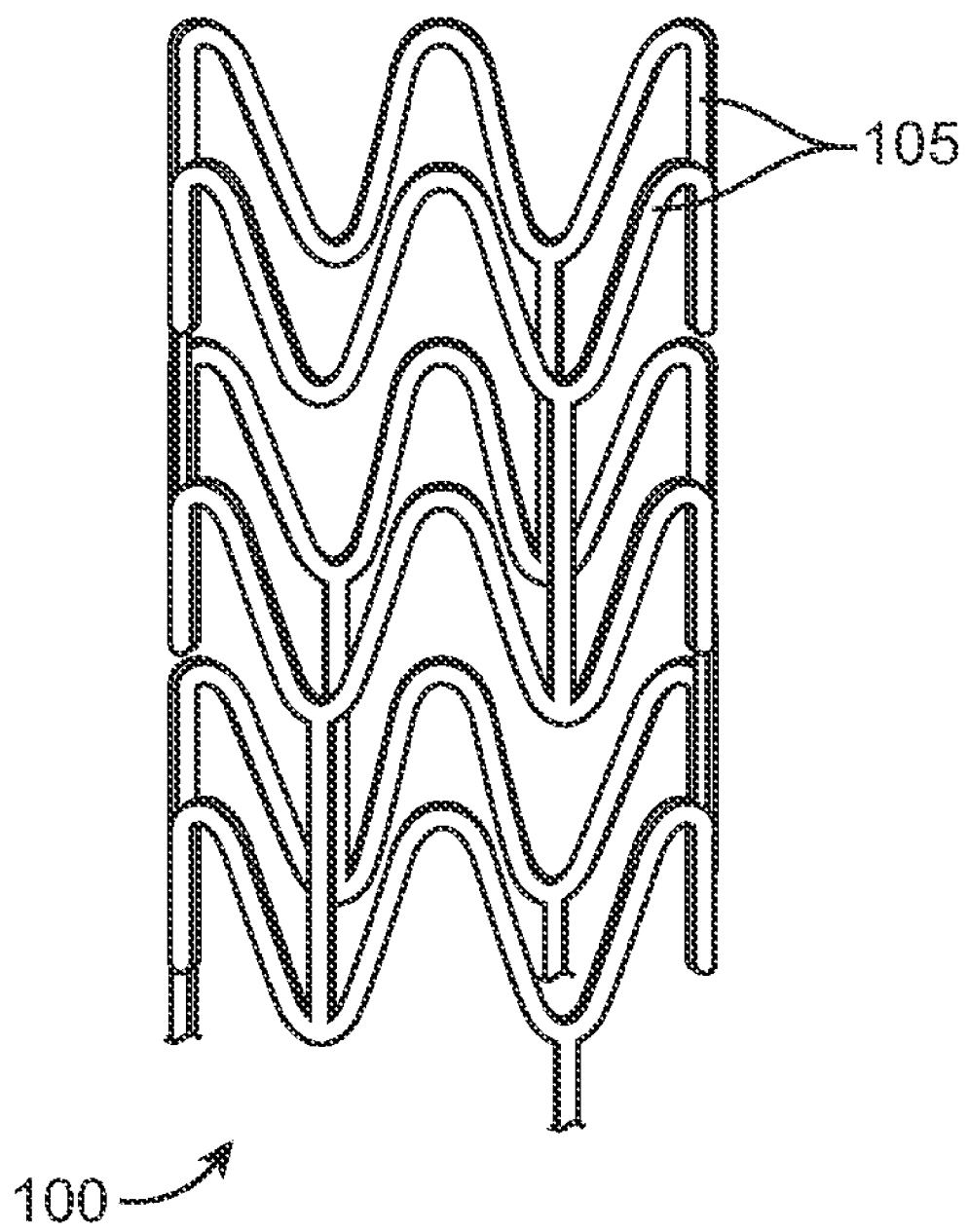
FIG. 1 depicts a stent.

FIG. 1 depicts a view of a stent 100. In some embodiments, a stent may include a body or scaffolding having a pattern or network of interconnecting structural elements 105. Stent 100 may be formed from a tube. The pattern of structural elements 105 can take on a variety of patterns. The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited. A stent such as stent 100 may be fabricated from a tube by forming a pattern with a technique such as laser cutting or chemical etching.

Furthermore, a stent can be designed for the localized delivery of a therapeutic agent. A medicated stent may be constructed by coating the device or substrate with a coating material containing a therapeutic agent. The substrate of the device may also contain a therapeutic agent.

An implantable medical device can be made partially or completely from a biodegradable, bioabsorbable, or biostable polymer. A polymer for use in fabricating an implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

Many biodegradable polymers that are candidates for stent materials degrade through hydrolytic mechanisms. Common examples of such biodegradable polymers are poly(hydroxy acids) such as poly(L-lactic acid), poly(DL-lactic acid), polyglycolide (PGA), poly(lactide-co-glycolide) (PLGA), and polycaprolactone (PCL), polyanhydrides, and polyarylates, among others.

Semi-crystalline biodegradable polymers, such as PLLA, may be selected as stent material due to strength and stiffness at physiological conditions so that a stent substrate or scaffolding can provide adequate support for a lumen. Physiological conditions refer to conditions within a human patient including, but not limited to, body temperature. Such polymers may be glassy or have a Tg above body temperature making them stiff and strong at body temperature which is approximately 37° C.

Some of these hydrolytically degradable polymers have potential shortcomings. One such shortcoming is that their degradation rate can be slower than desired for certain stent treatments. For example, a stent made from PLLA can have a degradation time of between about two and three years or longer (Medical Plastics and Biomaterials Magazine, March 1998, Medical Device Manufacturing & Technology 2005). As a result, the degradation time of a stent made from such a polymer can be longer than desired. "Degradation time" refers to the time for a stent implanted in a vessel to completely absorb. "Degradation time" can also refer to the time for a stent to completely absorb under in vitro conditions. In some treatment situations, a degradation time of less than 2 years may be desirable, for example, between 6 and 14 months, or more narrowly, between 8 and 12 months.

Reducing degradation time allows further surgery or intervention, if necessary, on a treated vessel to occur sooner. Additionally decreasing degradation time helps cut down on the cases of late stent thrombosis, a condition in which clots form on the surface of the stent months or years after deployment.

Additionally, the degradation byproducts produced by such polymers are frequently acidic. Such degradation byproducts can create a low pH environment in and around the polymer and result in an inflammatory response of neighboring tissue. The inflammatory response can increase as the degradation rate of the polymer increases. For example, the bulk degradation of such polymers as PLLA, PGA, and PLGA can result in a release of byproducts that facilitates inflammation.

Various embodiments of the present invention include a bioabsorbable stent with a stent scaffolding or body that is composed of two or more polymeric layers with different degradation rates. In these embodiments, the layers may be composed of polymeric materials that differ from layer to layer so that the degradation rates differ. As described in detail below, there are several ways of modifying polymer materials to change their degradation rate. Further embodiments of the present invention include a stent composed of layers that have been modified to have selected different degradation properties.

In some embodiments, the scaffolding has an inner or luminal layer, an outer or abluminal layer, and one or more middle layers between the abluminal and luminal layers. In such embodiments, the degradation rate of the stent scaffolding or body increases from the luminal to the abluminal layer. The layered geometry with staged degradation properties allows an increase in the degradation rate of the stent while minimizing or reducing the degree of inflammation caused by acidic degradation products. In particular, the staged degradation properties reduce or prevent release of acidic degradation properties in a shorter time range or burst release of byproducts that would result from a stent having uniformly high degradation rate.

In certain embodiments, the degradation rate of the luminal layer can be such that the luminal layer is capable of providing structural support to a lumen at least as long as a desired treatment time of the stent. Additionally, the degradation rate of the abluminal layer can be such that its degradation time is approximately or less than a desired treatment time of a stent. In exemplary embodiments, the degradation time of the luminal layer can be between 2-3 years and the degradation time of the abluminal layer can be less than about six months. In such embodiments, the degradation time of middle layer(s) can be between six months and two years, or more narrowly between 10 months and 14 months.

Additionally, as the faster degrading abluminal layer erodes, cell growth may proliferate on the abluminal surface of the scaffolding. Such cell grown can improve adhesion between the stent and the cell wall.

Figure 2A:
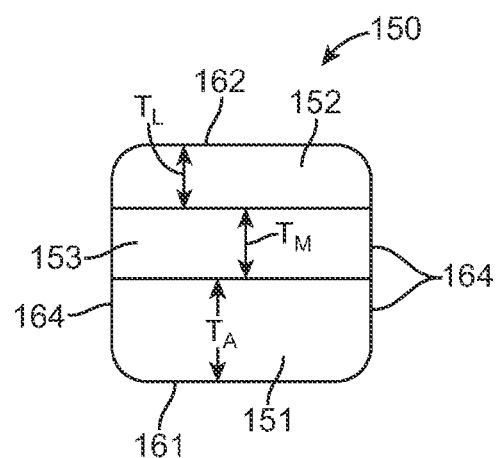
FIGS. 2A-B illustrate an exemplary embodiment of a strut or structural element of a stent composed of three layers.
Figure 2B:
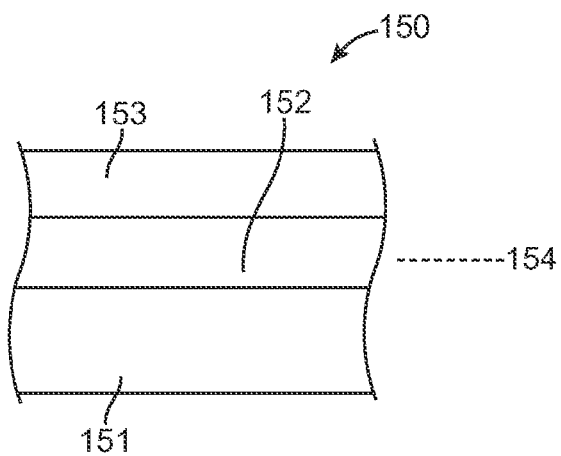
Figure 3:
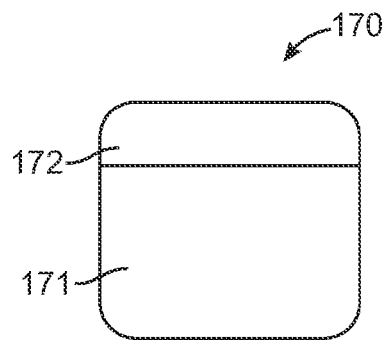
FIG. 3 illustrates another exemplary embodiment of a strut or structural element composed of two layers.

FIGS. 2A-B illustrate an exemplary embodiment of a strut or structural element composed of layers. FIGS. 2A-B depict a structural element 150 with a luminal layer 151, an abluminal layer 152, and a middle layer 153. FIG. 2A is a cross-section orthogonal to a longitudinal axis 154 of structural element 150 with a luminal surface 161, an abluminal surface 162, and sidewall surfaces 164. FIG. 2B depicts an axial cross-section of structural element 150. FIG. 3 illustrates another exemplary embodiment of a strut or structural element 170 composed of two layers, a luminal layer 171 and an abluminal layer 172.

A shown in FIG. 2A, luminal layer 151 has a thickness $T_A$, abluminal layer 152 has a thickness $T_L$, and middle layer 153 has a thickness $T_M$. $T_A$ may be large enough to allow luminal layer 151 to maintain support of a lumen even after middle layer 153 and abluminal layer 152 have eroded away or have lost or substantially lost mechanical properties due to degradation.

Luminal layer 151 is composed of a polymeric material that has a degradation rate slower than a degradation rate than the polymeric material of abluminal layer 152. Middle layer 153 is composed of a polymeric material with a degradation rate greater than the polymeric material of luminal layer 151 and less than the polymeric material of abluminal layer 153.

A stent having structural elements as depicted in FIGS. 2A-B and 3 can be fabricated by cutting a stent pattern in a tube with layers. FIG. 4A depicts a perspective view of a layered polymeric tube 180 with an outer surface 186 and cylindrical axis 185. The wall of tube 180 has three concentric or substantially concentric layers, an inner layer 181, an outer layer 182, and a middle layer 183. Layers 181, 182, and 183 are composed of different polymeric materials having different degradation rates, with the degradation rate increasing from the inner to the outer layer. FIG. 4B depicts a radial cross-section of tube 180 and FIG. 4C depicts a cross-section of the wall of tube 180 parallel to axis 185 of tube 180.

FIG. 5 depicts a radial cross-section of a stent scaffolding 190 cut from tube 180. Stent scaffolding 190 has structural elements 190A which have luminal layers 191, abluminal layers 192, and middle layers 193. In further embodiments, a stent scaffolding having two layers or having more than three layers can be formed from a tubes with the corresponding number of radial layers.

Various embodiments of the present invention can include a stent scaffolding with layers composed of polymer materials with different degradation rates. The polymer materials in the layers can have different degradation rates due to differences in molecular weight, composition of low molecular components, acidic end groups of polymers, and composition of faster degrading repeat units.

In general, the degradation rate of a polymer increases as its molecular weight decreases, which is due to several factors. Chain scission results in a larger number of smaller chain segments, many of which have acid end groups that can accelerate hydrolytic degradation reactions. Also, lower the molecular weight species tend to be more soluble. In addition, permeability of moisture through a polymer also increases as molecular weight decreases. As a result, there is an increase in uptake in water which further increases the degradation rate from increased hydrolysis.

In some embodiments, a molecular weight of the polymer material of the layers can be different so that there is a difference in the degradation rates of the layers. In such embodiments, the molecular weight decreases from the luminal to the abluminal layers so that the degradation rate of the layers increases from the luminal layer to the abluminal layer. In exemplary embodiments, each of the layers can be composed of or include a polymer of the same chemical composition or have the same repeat units. In the case of a copolymer, the copolymer of each of the layers can have the same composition of repeat units in each layer. In one embodiment, each of the layers can include or be composed of PLLA. In another embodiment, each of the layers can include or be composed of PLGA. The molecular weight of the polymer in a given layer varies from the luminal to the abluminal layer.

In general, a polymer and molecular weight of the polymer can be selected for a layer to obtain a desired degradation rate for a given layer. Table 1 lists the degradation times of several biodegradable polymers to provides a qualitative comparison of relative degradation times among the various biodegradable polymers.

TABLE 1

Degradation time of biodegradable polymers.

| Polymer | Degradation Time (months)[a] |
|---|---|
| PGA | 6-12[1,2] |
| PLLA | >24[1] |
|  | >36[2] |
| PDLLA | 12-16[1] |
|  | 12-15[2] |
| PCL | >24[1] |
|  | >36[2] |
| PDO | 6-12[1] |
|  | 6[2] |

[1]Medical Plastics and Biomaterials Magazine, March 1998.
[2]Medical Device Manufacturing & Technology 2005.
[a]Degradation time also depends on part geometry, dimensions, molecular weight In an exemplary embodiment of a three layer stent, the molecular weight of the polymer, such as PLLA, in each of the layers can provide degradation times of more than 3 years for the luminal layer, 2-3 years for middle layers, and less than 2 years for an abluminal layer. An exemplary embodiment of a two layer stent can have a molecular weight of the polymer, such as PLLA, in each of the layers that provides degradation times of 3 years or more for the luminal layer and less than 2 years for an abluminal layer. In exemplary embodiments, the molecular weight (Mw) of PLLA can be between 200 kg/mol and 1000 kg/mol in a luminal layer, between 20 kg/mol and 50 kg/mol in an abluminal layer, and between 50 kg/mol and 200 kg/mol in a middle layer.

Exemplary PLGA copolymers can include, but are not limited to, 95/5, 90/10, 85/15, 70/30, 65/35, and 50/50 L-lactide/glycolide copolymers, where 95/5, for example, refers to 95 wt % L-lactide and 5 wt % glycolide. Various commercial embodiments of biodegradable polymers, such as PLLA and PLGA, include polymers in the PURASORB® product line that can be obtained from Purac of Lincolnshire, Ill.

In another exemplary embodiment of a three layer stent, the molecular weight of the polymer, such as PLGA containing 15% GA, in each of the layers can provide degradation times of more than 2 years for the luminal layer, 1-1.5 year for middle layers, and less than 1 year for an abluminal layer. An exemplary embodiment of a two layer stent can have a molecular weight of the polymer, such as PLGA with 15% GA, in each of the layers that provides degradation times of 2 years for the luminal layer and less than 1 year for an abluminal layer. In exemplary embodiments, the Mw of PLGA can be between 200 kg/mol and 1000 kg/mol in a luminal layer, between 20 kg/mol and 50 kg/mol in an abluminal layer, and between 50 kg/mol and 200 kg/mol in a middle layer.

In further embodiments, the polymer in one or more of the layers, especially in the abluminal layer or middle layer(s), can include acidic end groups to further increase the degradation rate. As indicated above, the degradation rate of hydrolytically degradable polymers increases as the local pH of the polymer decreases. The rate of the hydrolysis reaction of water with a polymer increases as the pH of the local environment decreases. Additionally, acid groups tend to be hydrophilic which increases water uptake by the polymer, further increasing the hydrolysis reactions. In such embodiments, the acidic end groups can include carboxylic acid, —COOH. As the concentration of acidic end groups increases, the degradation of a layer increases.

In some embodiments, the concentration of acidic end groups can increase from the luminal to abluminal layers. In particular, the acidic end groups allow further increase the degradation rate of a layer beyond which is provided by a decrease in molecular weight. PLLA or PLGA with carboxylic acid end groups can be prepared through the acidification of PLLA or PLGA with hydroxyl end groups. Journal of Polymer Science: Part A: Polymer Chemistry, Vol. 39, 973-985 (2001).

Additional embodiments of the present invention can include layers composed of or including polymer materials having a high molecular weight polymer and different amounts of a low molecular component. The low molecular weight component tends to decrease the degradation rate of the polymer material of a layer. In some embodiments, the high molecular weight component is the same in each of the layers, for example PLLA or PLGA. In these embodiments, the composition of the low molecular weight component is lower in the luminal layer than the abluminal layer. The composition of the low molecular weight component in the middle layers can be between that of the luminal and abluminal layers. In certain embodiments, the composition of low molecular weight component can increase between the luminal layer and the abluminal layer.

In certain other embodiments, the high molecular weight component can be different in different layers. In such embodiments, the low molecular weight component can also be different in different layers. For example, the low molecular weight component of a given layer can have the same repeat units as the high molecular weight component. In these embodiments, the composition of the low molecular weight component in a layer can be adjusted to obtain a selected degradation rate. For instance, in an exemplary embodiment, a luminal layer can have PLLA as high and low molecular weight components. An abluminal layer can then have a polymer with repeat units that is faster degrading than PLLA, for example, polydioxanone (PDO) has a degradation time between 6-12 months (Medical Plastics and Biomaterials Magazine, March 1998). In some embodiments, the polymer material of the layers can be composed of at least 90, 95, or 99 wt % of the high molecular weight component. In one embodiment, the luminal layer may be 100 wt % of the high molecular weight component. In exemplary embodiments, the low molecular weight component can be 0-10 wt % of a layer or greater than 10 wt %.

In exemplary embodiments, the a high molecular weight polymer, such as PLLA or PLGA, can have a Mw between 200 kg/mol and 1000 kg/mol. The low molecular weight component can have a Mw between 2 kg/mol and 20 kg/mol. In some embodiments, the low molecular weight component has the same repeat units as the high molecular weight component.

In an exemplary embodiment, the layers of the stent body can include a high molecular weight PLLA or PLGA blended with a low molecular weight component. A three layer scaffolding can have a luminal layer with between 0-1 wt % of the low molecular weight component, an abluminal layer with between 5-10 wt % of the low molecular weight component, and a middle layer can have between 1-5 wt % of the low molecular weight component.

In other embodiments of the present invention, one or more layers can be composed of a copolymer that has a degradation rate that depends on the relative composition of its component repeat units. The degradation rate can vary due to the variation in composition of fast degrading units that are faster degrading than other slow degrading repeat units of the copolymer. "Faster degrading" refers to functional groups subject to hydrolytic degradation that hydrolyze faster than other repeat units subject to hydrolytic degradation in a copolymer.

In one embodiment, fast degrading units can correspond to functional units that form homopolymers that have a degradation time of less than a year. Slow degrading units can correspond to functional units that form homopolymers that have a degradation time greater than a year or two years. The dependence of degradation rate on composition of repeat units can also be due to the change in degree of crystallinity as the composition changes. In general, the degree of crystallinity is inversely related to the degradation rate of a polymer due to the increased diffusion of water through the polymer as crystallinity decreases.

In some embodiments, the composition of faster degrading repeat units in the copolymer of the abluminal layer and the luminal layer is such that the abluminal layer is faster degrading than the luminal layer. In addition, the composition of fast degrading repeat units in the copolymer of the middle layer can be such its degradation rate is between the copolymer in the luminal and abluminal layers. More generally, the composition of the fast degrading repeat units in the copolymer of the layers is such that the degradation rate increases from the luminal to the abluminal layers. In certain embodiments, the fast degrading repeat unit composition can range from 0-10 wt % to, 10-25 wt %, 25-50%, or greater than 50%.

In exemplary embodiments, layers of the stent body can include or be composed of PLGA. In such embodiments, the slow degrading units are L-lactide (LLA) and the fast degrading units are glycolide (GA). PGA is the simplest linear aliphatic polyester and degrades by hydrolysis of the easily accessible and hydrolytically unstable aliphatic-ester linkages. The degradation time depends on multiple factors like molecular weight, degree of crystallinity, crystal morphology, and physico-chemical characteristics of the environment. While structurally very similar to PGA, PLLA has some quite different chemical, mechanical and physical properties due to the presence of a pendant methyl group on the alpha carbon. The methyl group in PLLA makes the carbonyl of the ester link sterically less accessible to hydrolytic attack, which, depending on certain factors like the type of PLLA, its molecular weight, and its degree of crystallinity, makes the PLLA typically more hydrolytically stable than PGA when exposed to the same environment.

Figure 6:
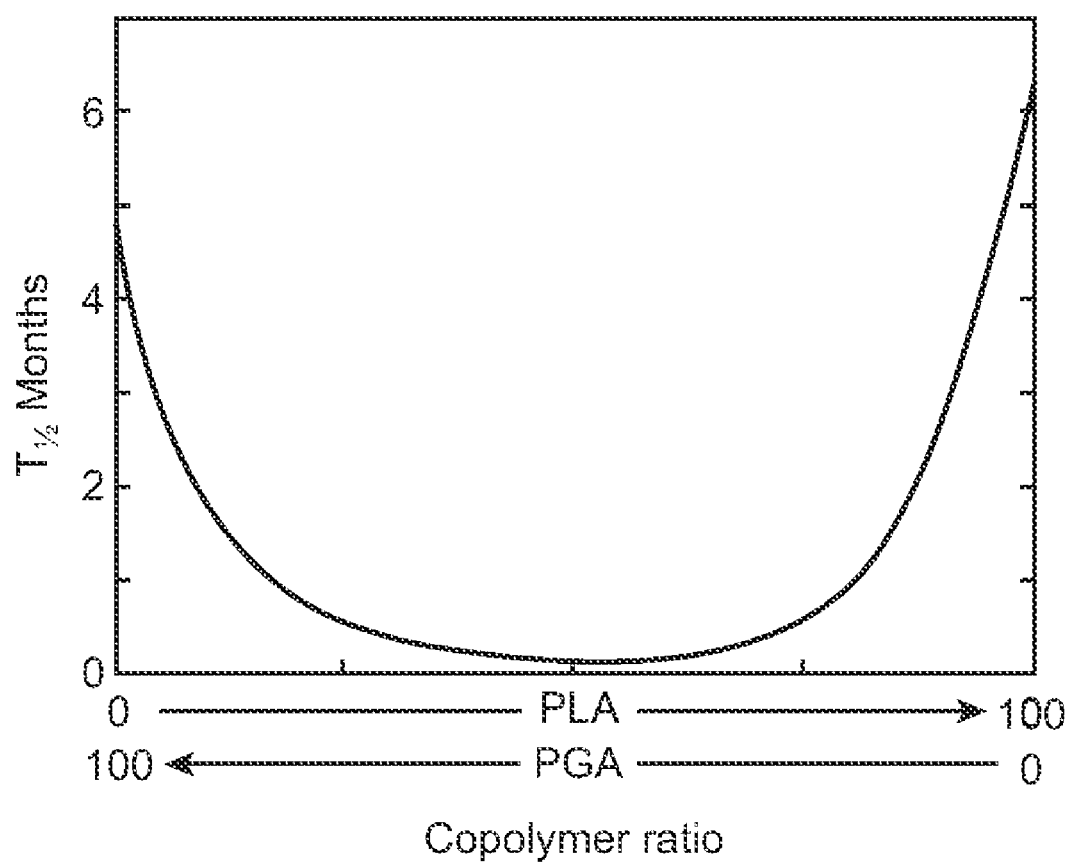
FIG. 6 shows the half-life of PLLA and PGA homopolymers and copolymers implanted in rat tissue.

Exemplary literature data shows PGA has a degradation time of between 6 and 12 months (See Table 2) while PLLA has a degradation time between 2 and 3 years (Table 1), thus there is an overall decrease in degradation rate as GA ranges between 0-100 wt %. However, as shown by Table 2, the degradation time of PLGA increases as the GA composition increases from 0 wt % and decreases from 100 wt %. FIG. 6 shows the half-life of PLLA and PGA homopolymers and PLGA copolymer implanted in rat tissue (Journal of Biomedical Materials Research, 11:711, 1977). The half-life in FIG. 6 refers to the amount of time for the modulus of a polymer to decrease by one half due to degradation of the polymer. Thus, it is expected that the degradation time exhibits a minimum between 40 wt % and 60 wt % GA.

TABLE 2

Degradation time of PLLA, PGA, and PLGA.

| Polymer | Degradation Time (months)[a] |
|---|---|
| PGA | 6-12[1,2] |
| PLLA | >24[1] |
|  | >36[2] |
| 85/15 PLGA | 5-6[1] |
| 75/25 PLGA | 4-5[1] |
| 65/35 PLGA | 3-4[1] |
| 50/50 PLGA | 1-2[1] |

[1,2,a]See Table 1

As shown in Table 2, the degradation time of PLGA decreases from 2 to 3 years (Table 1) to less than six months as the GA content increases from 0 wt % to 50 wt %. PLGA is amorphous throughout a wide range of GA content due to the disruption in the regularity in the polymer chain by the addition of another monomer. The decrease in degradation time is due both to the decreased crystallinity and increased hydrolytic activity of the GA.

In some embodiments, the PLGA of the layers has a GA composition between 0 wt % and 100 wt % and varies between the luminal layer and the abluminal layer so that the degradation rate increases between the luminal and abluminal layers. In an exemplary embodiments, the GA composition is less than 5 wt % or between 5-10 wt % in the luminal layer; at least 10 wt %, between 10-20 wt %, or 20-30 wt % in the abluminal layer; and between 10-30 wt % in a middle layer. In an exemplary embodiment, the luminal layer is PLLA, the abluminal layer is composed of PLGA with 30 wt % of GA, and a middle layer is composed of PLGA with 10 wt % GA.

As indicated above, a stent can be fabricated from a tube by laser machining a pattern into a tube. In certain embodiments, a tube with two or more layers having different polymer materials in the layers, as described above, can be formed by co-extrusion. In general, extrusion refers to the process of conveying a polymer melt through an extruder and forcing the polymer melt through a die that imparts a selected shape to the polymer exiting the extruder. In the case of tubing extrusion, the polymer melt (extrudate) forced through the die forms a cylindrical film in the shape of a tube. The film is cooled and drawn axially to form the final tube product.

An extruder generally includes a barrel through which a polymer melt is conveyed from an entrance to an exit port. The polymer can be fed to the extruder barrel in a solid form below its melting temperature. The solid polymer is melted as it is conveyed through the barrel. The polymer in the extruder barrel is heated to temperatures above the melting temperature (Tm) of the polymer and exposed to pressures above ambient. The polymer within the barrel is mixed, for example, through the use of rotating screws. Representative examples of extruders for use with the present invention may include single screw extruders, intermeshing co-rotating and counter-rotating twin-screw extruders and other multiple screw masticating extruders.

With respect to layers having a blend of high molecular weight polymer and a low molecular weight component, the blend corresponding to a particular layer can be fed to an extruder for forming the layered tubing. In other embodiments, the polymer components of a layer can be fed separately to the extruder and mixed or compounded within the extruder.

The polymer melt exits the extruder to a die placed at the end of the extruder barrel. A die generally refers to a device having an orifice with a specific shape or design geometry that it imparts to a polymer melt pumped from an extruder. In the case of tubing extrusion, the die has a circular shaped orifice that imparts a cylindrical shape to the polymer melt exiting the die. The function of the die is to control the shape of the polymer melt by delivering polymer melt to the orifice. The polymer melt can be delivered at a constant rate, temperature, and pressure.

Co-extrusion refers to the process of extruding two or more materials through a single die with two or more orifices arranged so that the extrudates from the separate orifices merge and weld together into a laminar structure before cooling or chilling. Each material can be fed to the die from a separate extruder, but the orifices may be arranged so that each extruder supplies two or more layers of the same material. In the case of tubing co-extrusion, the die can include concentric circular slits through which the different materials exit to form a tube with two or more layers.

Figure 7:
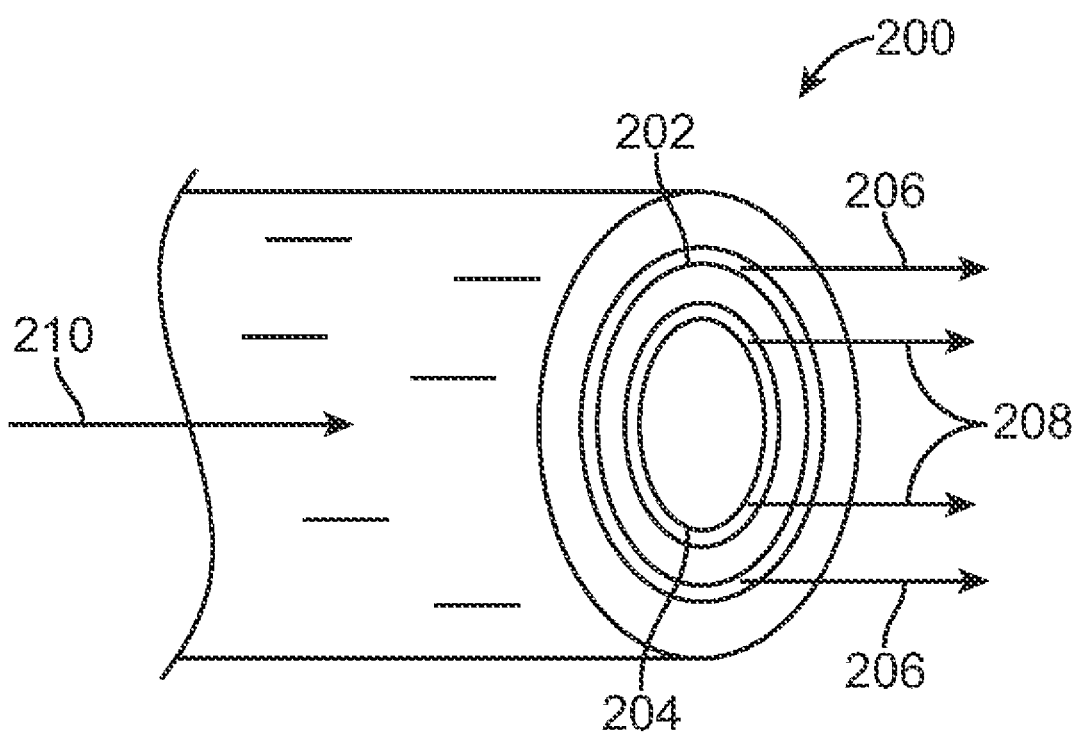
FIG. 7 depicts a die having two circular orifices, an outer orifice, and an inner orifice.

In some embodiments of the present invention, extrudates including polymer materials corresponding to desired layers of a stent body are formed in extruders and fed to a die with two or more circular orifices for formation of the layered tube. In an exemplary embodiment, FIG. 7 depicts a die 200 having two circular orifices, an outer orifice 202 and an inner orifice 204. An extrudate including a polymer material of an outer layer can exit through outer orifice 202, as shown by arrows 206, while an extrudate corresponding to an inner layer can exit through inner orifice 204, as shown by arrows 208. The extrudates are conveyed through die 200, in the direction of an arrow 210. The exiting extrudates merge and are welded together to form a cylindrical layered film which is cooled to form a tube.

Representative examples of polymers that may be used to fabricate an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), poly-orthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol. For the purposes of the present invention, the following terms and definitions apply:

As indicated above, an implantable medical device such as a stent can be medicated by incorporating an active agent in a coating over the device or within the substrate of the device.

For the purposes of the present invention, the following terms and definitions apply:

"Molecular weight" can refer to the molecular weight of individual segments, blocks, or polymer chains. "Molecular weight" can also refer to weight average molecular weight or number average molecular weight of types of segments, blocks, or polymer chains. The number average molecular weight (Mn) is the common, mean, average of the molecular weights of the individual segments, blocks, or polymer chains. It is determined by measuring the molecular weight of N polymer molecules, summing the weights, and dividing by N:

$$\overline{M}_n = \frac{\sum_i N_i M_i}{\sum_i N_i}$$

where Ni is the number of polymer molecules with molecular weight Mi. The weight average molecular weight is given by $$\overline{M}_w = \frac{\sum_i N_i M_i^2}{\sum_i N_i M_i}$$

where Ni is the number of molecules of molecular weight Mi.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

EXAMPLES

The examples and experimental data set forth below are for illustrative purposes only and are in no way meant to limit the invention. The following examples are given to aid in understanding the invention, but it is to be understood that the invention is not limited to the particular materials or procedures of examples. The Examples below are provided by way of illustration only and not by way of limitation. The parameters and data are not to be construed to limit the scope of the embodiments of the invention.

Example 1

Multi-Layer Stent Preparation from PLGA with 10 wt % GA with Different Mw and End Groups Three materials are used for co-extrusion. The first material is PLGA (90:10) with —OH end groups and Mw=600 kg/mol, which is used to form a luminal layer with about 2 years degradation time. The second material is PLGA (90:10) with —OH end groups and Mw=80 kg/mol, which is used to form middle layer with about 1.5 years degradation time. The third material is PLGA (90:10) with —COOH end groups and Mw=40 kg/mol, which is used to form abluminal layer with less than 1 year degradation time.

Step 1: Obtain 3-layer tubing through co-extrusion at 200° C. of the above three PLGA's (90:10) with different Mw's and end groups. The inside diameter (ID) of the extruded tubes is 0.02" and the outside diameter (OD) is 0.07". The thickness of the luminal and middle layers is 0.02" and is 0.01" for abluminal layer.

Step 2: Radially expand the extruded tubes to improve its mechanical property along the axial and radial directions. For the expanded tubing, control ID at 0.12" and OD at 0.13".

Step 3: Cut stents from the expanded tubes by femto second laser and sterilize all stents after crimping.

Example 2

Multi-Layer Stent Preparation from High Mw PLGA (85:15) with 15% GA with Different Mw and End Groups Three materials are used for co-extrusion. The first material is pure PLGA (85:15) with —OH end groups and Mw=600 kg/mol, which is used to form the luminal layer with about 1.5 years degradation time. The second material is a mixture (100:5 wt % ratio) of high Mw (600 kg/mol) and low Mw (10 kg/mol) PLGA (85:15) with —OH end group, which is used to form the middle layer with less than 1 year degradation time. The third material is a mixture (100:10 wt % ratio) of high Mw (600 kg/mol) and low Mw (5 kg/mol) PLGA (85:15) with —COOH end group, which is used to form the abluminal layer with less than six months degradation time.

Step 1: Obtain 3-layer tubing through co-extrusion at 200° C. of the above three materials. The ID of the extruded tubes is 0.02" and the OD is 0.07". The thickness of the luminal and middle layers is 0.02" and is 0.01" for abluminal layer.

Step 2: Expand the extruded tubes to improve its mechanical property along the axial and radial directions. For the expanded tubing, control ID at 0.12" and OD at 0.13".

Step 3: Cut stents from the expanded tubes by femto second laser and sterilize all stents after crimping.

Example 3

Multi-Layer Stent Preparation from High Mw PLGA with Different GA Content

Three materials are used for co-extrusion. The first material is PLGA (85:15) with —OH end group and Mw=500 kg/mol, which is used to form the luminal layer with about 1.5 years degradation time. The second material is PLGA (75:25) with —OH end groups and Mw=500 kg/mol, which is used to form the middle layer with less than 1 year degradation time. The third material is a PLGA (50:50) with —OH end groups and Mw=500 kg/mol, which is used to form the abluminal layer with less than six months degradation time.

Step 1: Obtain 3-layer tubing through co-extrusion at 200° C. of the above three PLGAs with different GA content. The ID of the extruded tubes is 0.02" and the OD is 0.07". The thickness for the luminal layer and middle layer is 0.02" for and is 0.01" for the abluminal layer.

Step 2: Expand the extruded tubes to improve its mechanical property along the axial and radial directions. For the expanded tubing, control ID at 0.12" and OD at 0.13".

Step 3: Cut stents from the expanded tubes by femto second laser and sterilize all stents after crimping.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention

What is claimed is:

1. A bioabsorbable stent comprising a stent scaffolding comprising:
   an abluminal layer, a luminal layer, and optionally one or more middle layers,
   each layer comprising a glassy degradable polymer of the same chemical composition,
   wherein the abluminal layer is an outermost radial layer of the stent scaffolding with an outer surface contacting a vessel wall upon implantation,
   wherein the luminal layer is an innermost radial layer of the stent scaffolding with an inner surface contacting an inner lumen of the vessel upon implantation,
   wherein the molecular weight of the polymer of the luminal layer is higher than the molecular weight of the polymer of the abluminal layer, and
   wherein the molecular weight of the polymer of the layers decreases between each of the layers from the luminal layer to the abluminal layer so that the degradation rate of the layers increases between each of the layers from the luminal layer to the abluminal layer.

2. The stent of claim 1, wherein the polymer in one or more of the layers has —COOH end groups.

3. The stent of claim 1, wherein the polymer comprises PLLA or PLGA.

4. The stent of claim 1, wherein the scaffolding comprises a middle layer, the polymer of a middle layer comprising a Mw between 50 kg/mol and 200 kg/mol.

5. The stent of claim 1, wherein the scaffolding comprises a middle layer, the luminal layer completely absorbing in about 2-3 years, the middle layer completely absorbing in about 1-1.5 year, and the abluminal layer completely absorbing in less than 1 year.

6. The stent of claim 1, wherein the scaffolding comprises a middle layer, the luminal layer completely absorbing in at least 3 years, the middle layer completely absorbing in about 2-3 years, and the abluminal layer completely absorbing in less than 1 year.

7. A bioabsorbable stent comprising a stent scaffolding including:
   an abluminal layer, a luminal layer, and at least one middle layer,
   wherein the abluminal layer is an outermost radial layer of the stent scaffolding with an outer surface contacting a vessel wall upon implantation,
   wherein the luminal layer is an innermost radial layer of the stent scaffolding with an inner surface contacting an inner lumen of the vessel upon implantation,
   wherein the luminal layer comprises PLLA or PLGA and the abluminal layer and the at least one middle layer comprises PLGA,
   wherein the GA content of the abluminal layer is higher than the GA content of the luminal layer, and
   wherein the GA content of the polymer of the layers increases between each of the layers from the luminal layer to the abluminal layer so that the degradation rate between each of the layers increases between each of the layers from the luminal layer to the abluminal layer.

8. The stent of claim 7, wherein the luminal layer completely absorbing in less than 2 or 3 years, the middle layer completely absorbing in less than 1 year, and the abluminal layer completely absorbing in less than six months.

* * * * *